United States Patent
Anapliotis et al.

(10) Patent No.: US 9,675,462 B2
(45) Date of Patent: Jun. 13, 2017

(54) INTERMEDIATE BODY FOR A BONE IMPLANT, AND IMPLANT ARRANGEMENT

(71) Applicant: Merete Medical GmbH, Berlin (DE)

(72) Inventors: Emmanuel Anapliotis, Berlin (DE); Guenter Lob, Munich (DE)

(73) Assignee: Aristotech Industries GmbH, Luckenwalde (DE)

( * ) Notice: Subject to any disclaimer, the term of this patent is extended or adjusted under 35 U.S.C. 154(b) by 0 days.

(21) Appl. No.: 14/758,658

(22) PCT Filed: Feb. 7, 2014

(86) PCT No.: PCT/DE2014/100044
§ 371 (c)(1),
(2) Date: Jun. 30, 2015

(87) PCT Pub. No.: WO2014/121789
PCT Pub. Date: Aug. 14, 2014

(65) Prior Publication Data
US 2015/0335435 A1    Nov. 26, 2015

(30) Foreign Application Priority Data

Feb. 11, 2013 (DE) .................. 10 2013 101 325

(51) Int. Cl.
*A61F 2/28* (2006.01)
*A61F 2/32* (2006.01)
(Continued)

(52) U.S. Cl.
CPC .................. *A61F 2/32* (2013.01); *A61F 2/28* (2013.01); *A61F 2/36* (2013.01); *A61F 2/367* (2013.01);
(Continued)

(58) Field of Classification Search
CPC .... A61F 2/3641; A61F 2/3672; A61F 2/3674; A61F 2/30739; A61F 2002/3641; A61F 2002/3674
See application file for complete search history.

(56) References Cited

U.S. PATENT DOCUMENTS 4,938,768 A * 7/1990 Wu .................. A61B 17/68
                                                                403/307
5,569,263 A * 10/1996 Hein .................. A61B 17/1659
                                                                606/102
(Continued)

FOREIGN PATENT DOCUMENTS

DE       10308141 A1    10/2004
EP        0920289 B1    11/2002
(Continued)

OTHER PUBLICATIONS

International Preliminary Report on Patentability with English translation, PCT/DE2014/100044, date of issuance Aug. 11, 2015.
(Continued)

*Primary Examiner* — Thomas J Sweet
*Assistant Examiner* — Megan Wolf
(74) *Attorney, Agent, or Firm* — Andrus Intellectual Property Law, LLP

(57) ABSTRACT

An intermediate body is for a bone implant for replacement of an osseous area. The intermediate body has a base body and a seat which extends axially in the base body and is surrounded by a wall of the base body. The intermediate body is designed to receive and surround an end portion of an intramedullary implant part. A clamp device is assigned to the seat. A clamp component is arranged on the wall of the base body surrounding the seat. In order to clamp, the end portion is inserted beforehand into the seat relative to the wall of the base body. The wall then surrounds the seat and the inserted end portion is movable towards the seat and in
(Continued)

Figure 1:
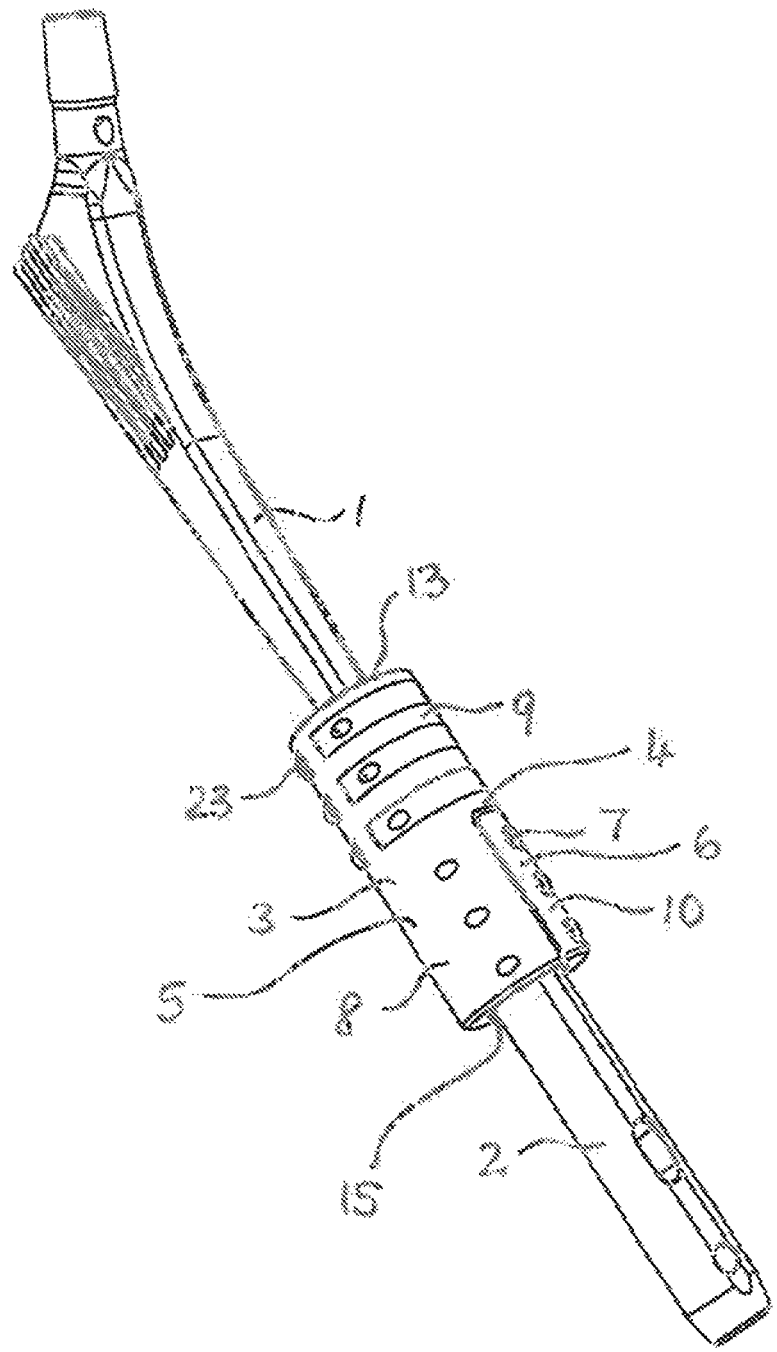

the process clamps the end portion in the seat. An implant arrangement is provided with the intermediate body.

20 Claims, 11 Drawing Sheets

(51) Int. Cl.
*A61F 2/36* (2006.01)
*A61B 17/72* (2006.01)
*A61F 2/30* (2006.01)

(52) U.S. Cl.
CPC ......... *A61F 2/3609* (2013.01); *A61F 2/3676* (2013.01); *A61B 17/72* (2013.01); *A61F 2/3672* (2013.01); *A61F 2002/2825* (2013.01); *A61F 2002/2832* (2013.01); *A61F 2002/3038* (2013.01); *A61F 2002/30331* (2013.01); *A61F 2002/30354* (2013.01); *A61F 2002/30382* (2013.01); *A61F 2002/30474* (2013.01); *A61F 2002/30487* (2013.01); *A61F 2002/3652* (2013.01); *A61F 2002/3674* (2013.01)

(56) References Cited

U.S. PATENT DOCUMENTS

| | | | |
|---|---|---|---|
| 6,454,810 B1* | 9/2002 | Lob | A61B 17/72 606/62 |
| 8,287,598 B1 | 10/2012 | Doty | |
| 2003/0204269 A1 | 10/2003 | Gerbec et al. | |
| 2006/0129247 A1 | 6/2006 | Brown et al. | |
| 2011/0144756 A1* | 6/2011 | Bickley | A61F 2/40 623/18.11 |
| 2011/0196503 A1 | 8/2011 | Anapliotis et al. | |
| 2013/0006358 A1 | 1/2013 | Olevsky et al. | |
| 2013/0085577 A1* | 4/2013 | Link | A61F 2/3607 623/23.39 |

FOREIGN PATENT DOCUMENTS

| | | | |
|---|---|---|---|
| WO | 2010025704 A1 | 3/2010 | |
| WO | WO 2011154156 A1 * | 12/2011 | ........... A61F 2/3607 |

OTHER PUBLICATIONS

International Search Report for PCT/DE2014/100044 dated Jun. 6, 2014.

* cited by examiner

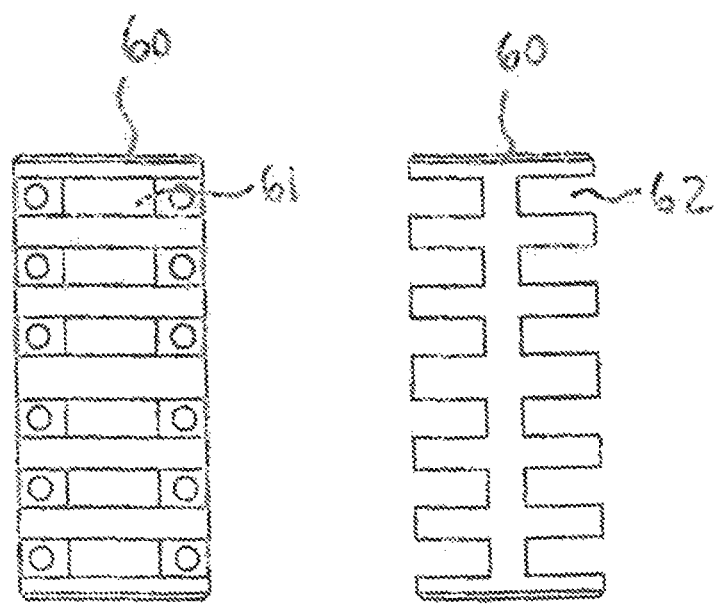
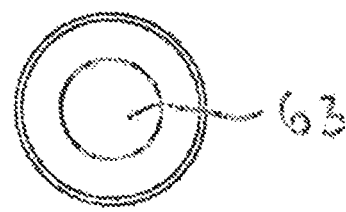
Fig. 6

INTERMEDIATE BODY FOR A BONE IMPLANT, AND IMPLANT ARRANGEMENT

CROSS-REFERENCE TO RELATED APPLICATIONS

This application is the U.S. national stage application of International Application PCT/DE2014/100044, filed Feb. 7, 2014, which international application was published on Aug. 14. 2014, as International Publication WO2014/121789. The international application is incorporated herein by reference, in entirety. The international application claims priority to German Patent Application No, 102013101325.2, filed Feb. 11, 2013 which is incorporated herein by reference, in entirety.

The invention relates to an intermediate body for an implant for replacing an osseous area, and to an implant arrangement.

BACKGROUND

Document EP 0 920 289 B1 discloses an endoprosthesis in which an intermediate body with a cylindrical base body is provided, in which a seat extends axially through the base body in such a way that an endoprosthesis part is insertable into the seat via inlet openings at both ends. The base body is formed with two half-shells which, in the assembled state, lie parallel to each other along a center plane and are connected to each other by tensioning means in the form of screws. With the aid of the screws, the inserted end portion of the endoprosthesis part is then also clamped and, in this way, is fixed in its relative position to the base body.

A comparable intermediate body for an endoprosthesis is known from document US 2011/0196503 A1. The known intermediate body can be produced with a different axial overall length. An intermediate connector can be provided in order to form different overall lengths of the intermediate body connecting end portions of endoprosthesis parts.

Document WO 2010/025704 A1 discloses a knee arthrodesis implant in which an intermediate body connecting prosthesis parts is formed with two portions angled relative to each other.

SUMMARY

The object of the invention is to make available an intermediate body for an implant for replacing an osseous area, and also an implant arrangement, in which intermediate body and implant part(s) or implant portion(s) are connectable with improved mechanical stability, particularly also in the case of a non-cylindrical end portion of the implant part or implant component, for example of an endoprosthesis part.

To achieve the object, the invention proposes an intermediate body for an implant for replacing an osseous area in the diaphyseal and/or metaphyseal area of a bone as claimed in independent claim 1, and also an implant arrangement as claimed in independent claim 15. Advantageous embodiments are the subject matter of dependent claims.

According to one aspect, an intermediate body is proposed for an implant for replacing an osseous area, for example in the diaphyseal and/or metaphyseal area of a bone. The intermediate body has a base body, in which a seat extends in the axial direction. The seat is designed to receive and surround at least one end portion of an intramedullary implant part or implant component that can be inserted into the seat through an inlet opening. The seat is surrounded by a wall, which is formed as part of the base body. The wall surrounding the seat can be complete or interrupted about its periphery, for example with one or more wall slits extending in the longitudinal direction of the base body.

A clamp device assigned to the seat and having a clamp component is then provided. The clamp component is arranged on the wall of the base body surrounding the seat and, in order to clamp the end portion of the implant part inserted beforehand into the seat relative to the wall of the base body, which wall surrounds the seat and the end portion inserted therein, is movable toward the seat and in the process clamps the end portion in the seat.

Therefore, in contrast to the prior art, the fixing of the end portion of the intramedullary implant part or implant component in the seat formed on the base body is not effected at all, or not effected exclusively, with the aid of the wall of the base body itself, but instead exclusively or additionally by means of the clamp device, which has at least one clamp component with which the end portion of the implant part inserted beforehand into the seat on the base body is then fixed in the seat. Provision can be made here that the inserted end portion is already pre-clamped and is then finally fixed by means of the clamp component. Alternatively, provision can be made that the fixing of the end portion in the seat is effected exclusively with the aid of the clamp device, in particular with the movable clamp component.

According to a further aspect, an implant arrangement with such an intermediate body is created in which an end portion of an intramedullary implant part such as a joint prosthesis or nail is inserted into the seat in the base body and is fixed therein by means of clamping. A further seat can be formed on the base body, in such a way that a respective end portion of an intramedullary implant part can be inserted into the seat and into the further seat from opposite end faces of the base body and can be fixed therein by means of clamping.

The end portion of the intramedullary implant part can have a wide variety of shapes, particularly in respect of the cross section, for example round or angular.

The seat formed in the base body can be designed as a passage extending in the axial direction of the base body. Alternatively, the base body has two receiving pockets which issue respectively from the opposite end faces and which are separated from each other inside the base body by means of a separating portion, for example a partition wall extending transversely with respect to the axial direction of the base body.

The seat can be cylindrical in the different embodiments. A tapering cross section of the seat can also be provided. In this way, for example, a conically extending receiving pocket can be formed.

When moved into the clamping position, i.e. toward the seat, thereby clamping the end portion in the seat, the clamp component forming part of the clamp device can be moved into the seat itself, at least partially, for example with a front portion directed toward the seat. In this way, the cross section of the seat is then reduced at least locally by means of the clamp component being moved into this seat.

The clamp device can be designed as a steplessly adjustable clamp device, in which the clamp components are steplessly adjustable during the movement into and out of the clamping position.

The movement of the clamp component preferably takes place at least transversely with respect to the axial direction of the base body. In this way, the clamp component can, for example, be moved from the side into the axially extending seat, in order thereby to clamp and fix the inserted end portion in the seat, for example by means of pressing against an opposite portion of the wall surrounding the seat.

To forcibly move the clamp component into and out of the clamping position, a screw element can be provided, for example, which is screwable into the base body and which is screwed into an associated threaded bore in the wall.

In one embodiment, one or more clamp components of the clamp device can themselves be designed as screw elements, which are received in associated threaded bores in the wall surrounding the seat and, by means of turning them, can be screwed in toward the seat or can be moved away from the latter. Provision can be made here that the one or more screw elements press against a screw clamp element with their proximal end (foot) relative to the seat, which proximal end is movable toward and away from the seat, and the screw clamp element, at least in the clamping position, presses against the end portion of the intramedullary implant part arranged in the seat, such that the proximal end of the screw element, by way of the screw clamp element, presses against the inserted end portion. With the aid of the clamp element, the foot of the screw element can be broadened in order thereby to make available a larger clamping surface. The screw clamp element can be arranged tiltably at the proximal end, either releasably or non-releasably with respect to the screw element, for example using a ball-head mounting. On a side directed toward the seat, the screw clamp element can be provided with a curved surface.

The wall of the base body surrounding the seat can be designed in one piece. The base body can have a multi-part design as a whole, or also only in the area of the wall surrounding the seat, wherein this multi-part design is formed without the elements of the clamp device. The base body can be formed with two half-shells, which are connected to each other with the aid of connecting means, for example one or more screws. In one embodiment, the base body can be formed with the aid of two half-shells in one area of its axial extent, for example in half, whereas the base body, in another area of its axial extent, is designed in one piece about its periphery, for example in such a way that the seat here is surrounded by a one-piece, peripheral wall. Particularly in the case of a different design of the two halves of the base body, a partition wall for separating two receiving pockets at the ends can be provided in the interior.

In one embodiment, provision can be made that the clamp component, at least in a clamping position, is arranged at least partially in an associated clamp component seat in the area of the surrounding wall of the base body. The clamp component seat can be formed, for example, with a gap or slit for the clamp component to be received therein. The clamp component can be arranged with a form fit in the clamp component seat, at least in the clamping position. In one embodiment, the clamp component seat has a depression which is formed transversely with respect to the axial direction of the base body and which extends from the outer surface of the base body into the latter. Here, the clamp component can be moved between a clamping position and a released position, wherein the clamp component in the released position frees the end portion of the intramedullary implant part. Several identically or differently configured clamp component seats can be provided in one or both end portions of the intermediate body. The clamp component seats can differ, for example, in terms of their respective overall width. The overall width of the clamp component seats can be identical or different for the clamp component seats formed on one side of the intermediate body. A central portion of the intermediate body can be free of clamp component seats.

The clamp component can be received releasably on the surrounding wall. Alternatively, the clamp component is mounted non-releasably thereon, while maintaining its relative mobility with respect to the wall of the base body.

A refinement provides that the clamp component is movable into the seat in order to clamp the end portion inserted beforehand into the seat. In this embodiment, a portion of the clamp component facing toward the seat is arranged, at least in the clamping position, in the seat formed in the base body and there clamps the end portion inserted into the seat.

The clamp device can have several clamp components, which are arranged on the wall of the base body surrounding the seat and which, in order to clamp the end portion inserted beforehand into the seat relative to the wall of the base body, which wall then surrounds the seat and the inserted end portion, are movable independently of each other, are at least partly in unison, toward the seat and in the process clamp the end portion in the seat. The several clamp components can be arranged releasably or non-releasably in the area of the wall of the base body surrounding the seat. The several clamp components can be configured identically or differently, particularly in terms of their external shape.

In order to fix the end portion of the implant part or implant component, the one or more clamp components can cooperate with one or more mating clamp components which can be arranged lying opposite in the area of the seat. Provision can be made here that, with the aid of tensioning means, for example one or more screws, clamp component and mating clamp component are moved jointly toward each other into the clamping position, such that in this way the end portion of the implant part is fixed in the seat. Alternatively, the end portion of the implant part can also be pressed with the aid of the clamp component, at least locally, against a wall portion of the base body lying opposite the clamp component.

In one development, provision can be made that, for the several clamp components, individual and mutually different clamp widths can be set in the seat. In this way, different clamp widths or clamp cross sections can be set locally in the seat for the several clamp components. For example, the clamp width or the clamp cross section can taper in the seat from the end toward the center. This is advantageous, for example, if a conically extending end portion of a hip-joint endoprosthesis is intended to be received and fixed in the intermediate body. However, it is not only conical end portions, but also any non-cylindrical end portions of implant parts, for example a shaft or a nail, that can advantageously be fixed in this way in the intermediate body for the endoprosthesis. In this embodiment or other embodiments, the several clamp components can be of identical or different shape. With the aid of different shaping, the clamp cross section provided by the respective clamp component in the seat can be adapted.

In a preferred development, provision is made that the several clamp components form an arrangement of clamp elements extending in the axial direction of the base body, which clamp elements can optionally be arranged adjacent to each other. The several clamp components can be arranged next to each other in the longitudinal direction of the base body, either at regular or irregular intervals. Here, each of the clamp components can be arranged in an associated clamp component seat. It is also possible for several clamp components to be mounted in a common clamp component seat.

The arrangement of clamp elements extending in the axial direction of the base body can be formed over the entire length of the base body.

In an expedient embodiment, provision can be made that the one or more clamp components have, on a side facing toward the seat, a superficial clamp structure. The superficial clamp structure can have clamping jaws, clamping projections and/or depressions. The superficial clamp structures are preferably arranged frontally on the clamp component, in such a way that, in the clamping position, the superficial clamp structure presses against an opposite surface of the clamped end portion of the implant part. The superficial clamp structure can be different for the several clamp components. For example, the superficial clamp structure can have a depression whose cross section is greater for a clamp component proximal to the end face of the base body than for a comparative clamp component distal to the end face. In this way, a groove of decreasing or increasing cross section can be formed in the seat along the clamp components, on which groove the end portion of the intramedullary implant part can then be placed during clamping.

In an advantageous embodiment, provision is made that an anti-slip surface profiling is formed on an inner face of the wall surrounding the seat. The anti-slip surface profiling can engage with profiles on the surface of the end portion of the implant part.

In one refinement, provision is preferably made that the clamp device is formed with tensioning elements, with which clamping forces oriented transversely with respect to each other can be developed, for example in different areas of the base body. For example, the clamping forces can be oriented at an angle of about 90° to each other. Provision can be made that the clamping forces oriented transversely with respect to each other are made available with the aid of screw elements that extend transversely with respect to each other. Thus, the screw direction in one half of the base body can be transverse to the screw direction in the other half of the base body.

In one embodiment, provision can be made that the one or more clamp components have a multi-part design. A multi-part design of the clamp components is present, for example, if the clamp component is assigned a mating component which is arranged, lying opposite the clamp component, in the area of the wall of the base body surrounding the seat. Mutually associated clamp components of this kind can have superficial clamp structures in mirror image with respect to the center axis. One or more common tensioning means, for example one or more screws, can be provided for moving clamp component and mating clamp component toward each other to the clamping position.

In one development, provision can be made that the one or more clamp components are each formed with a screw element that is screwed into the wall of the base body surrounding the seat. For example, a respective screw can be received in an associated threaded bore. In this way, in one embodiment, an adjustable and to this extent individually configurable seat for securing prosthesis parts of any desired shaft geometry can be made available in both end areas of the base body.

DESCRIPTION OF ILLUSTRATIVE EMBODIMENTS

Figure 2:
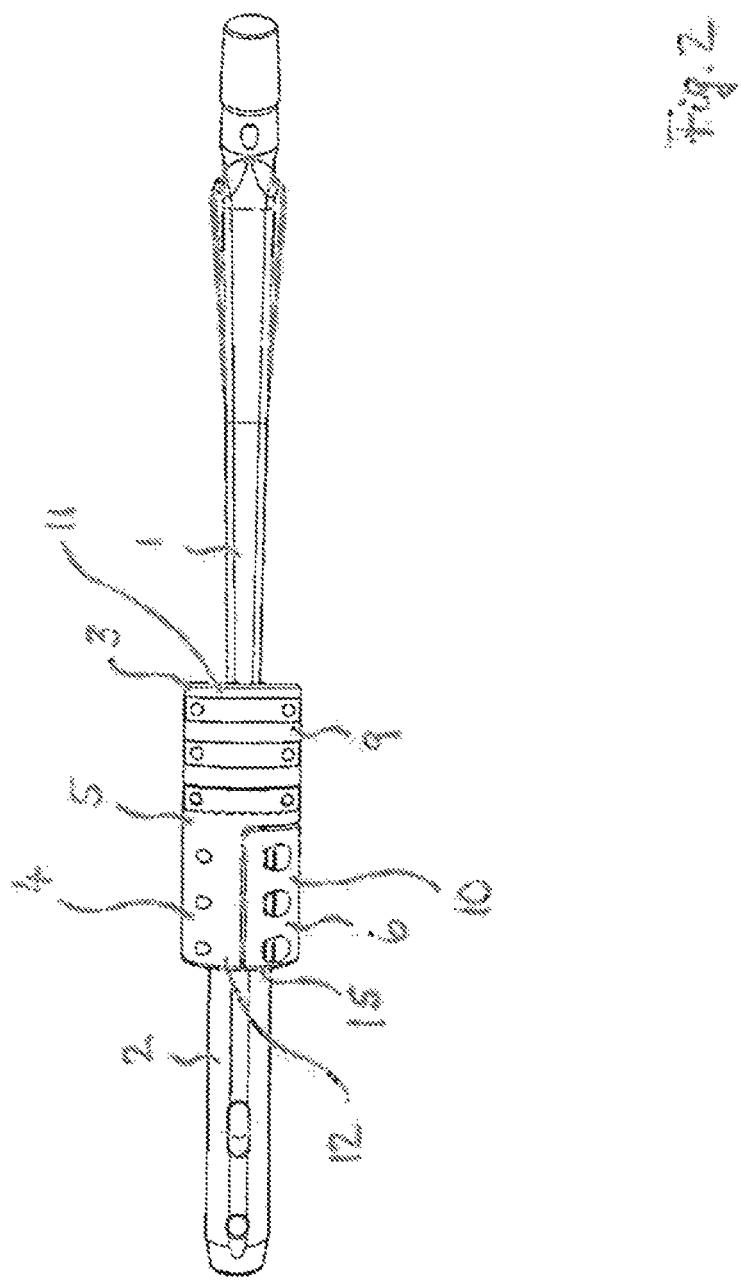
Figure 3:
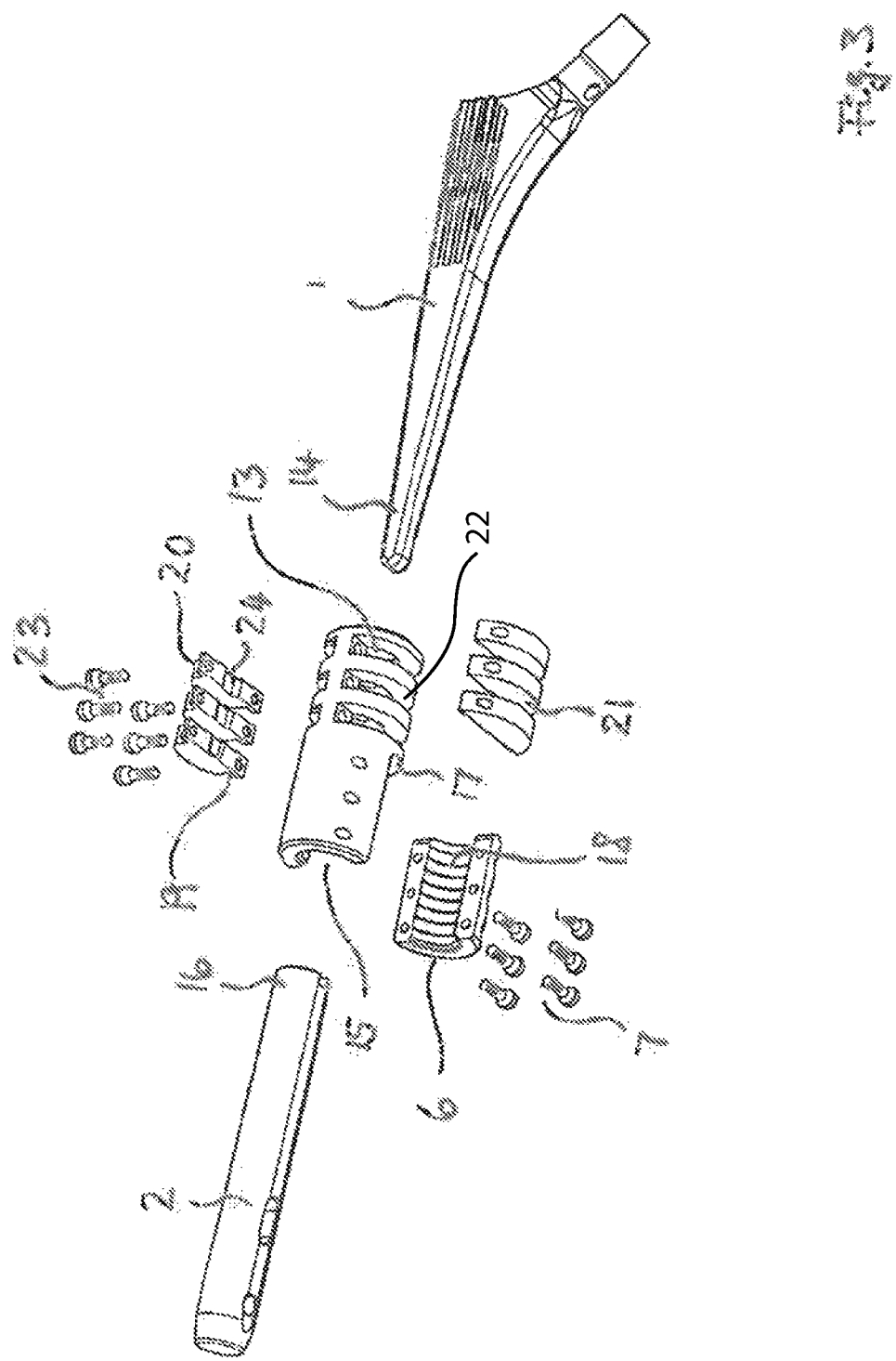
Figure 4:
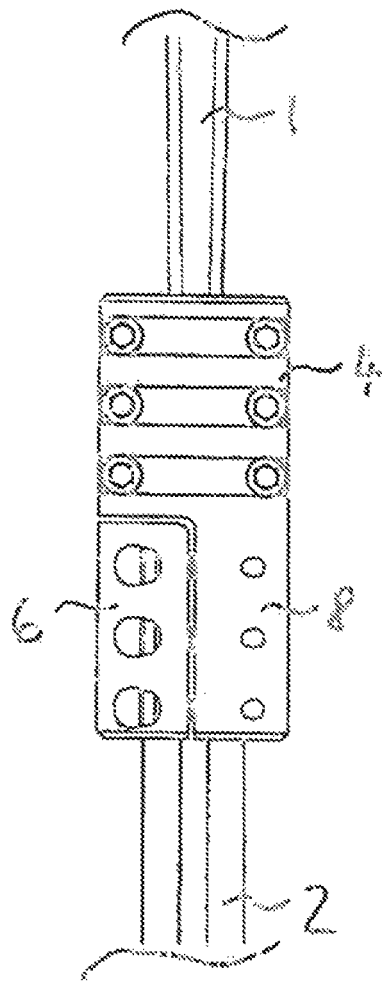
Figure 5:
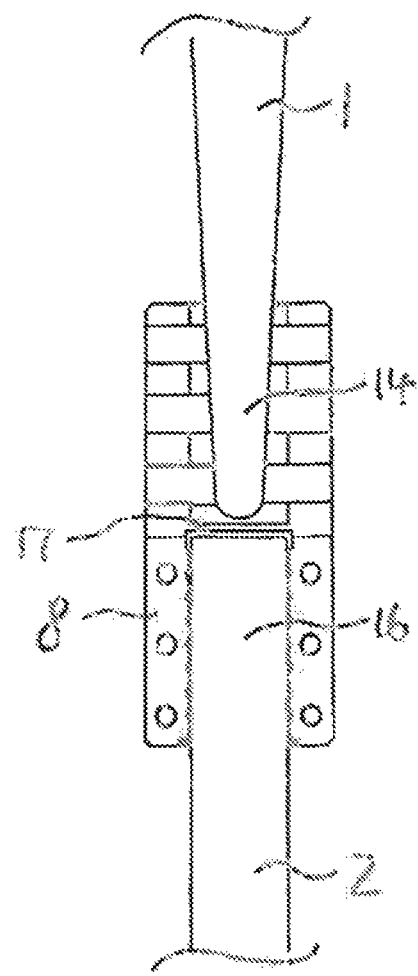
Figure 7:
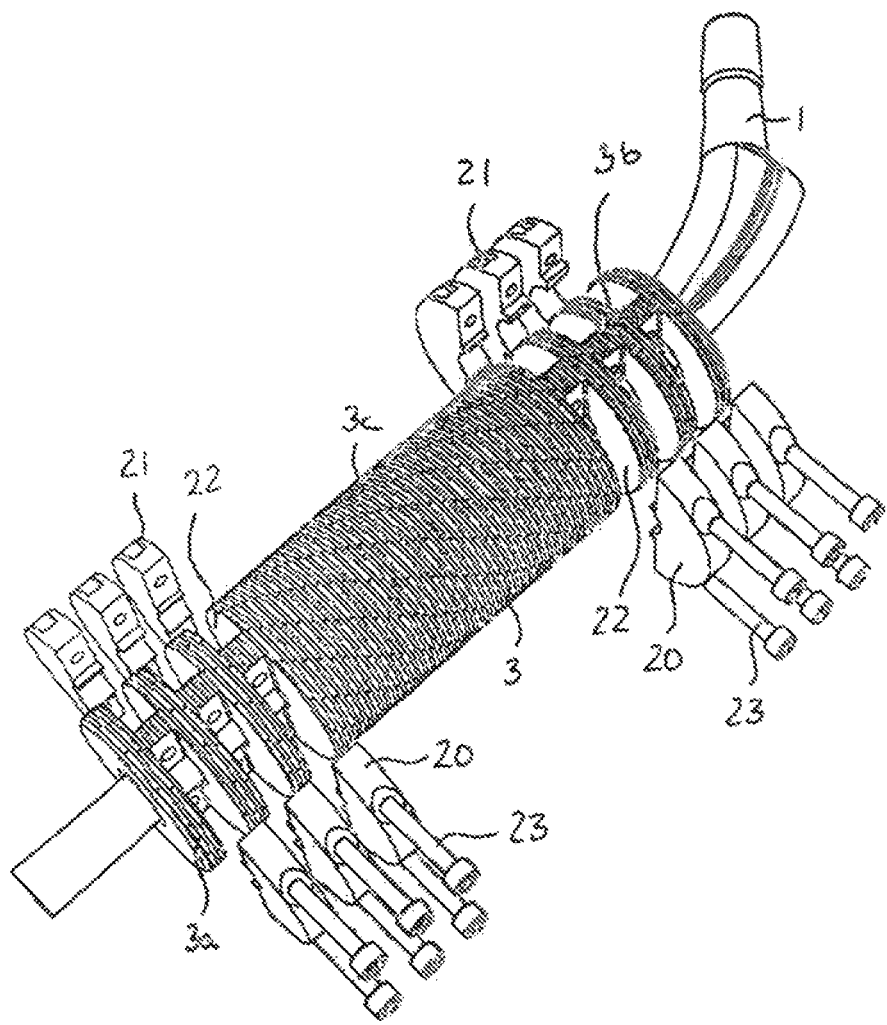
Figure 8:
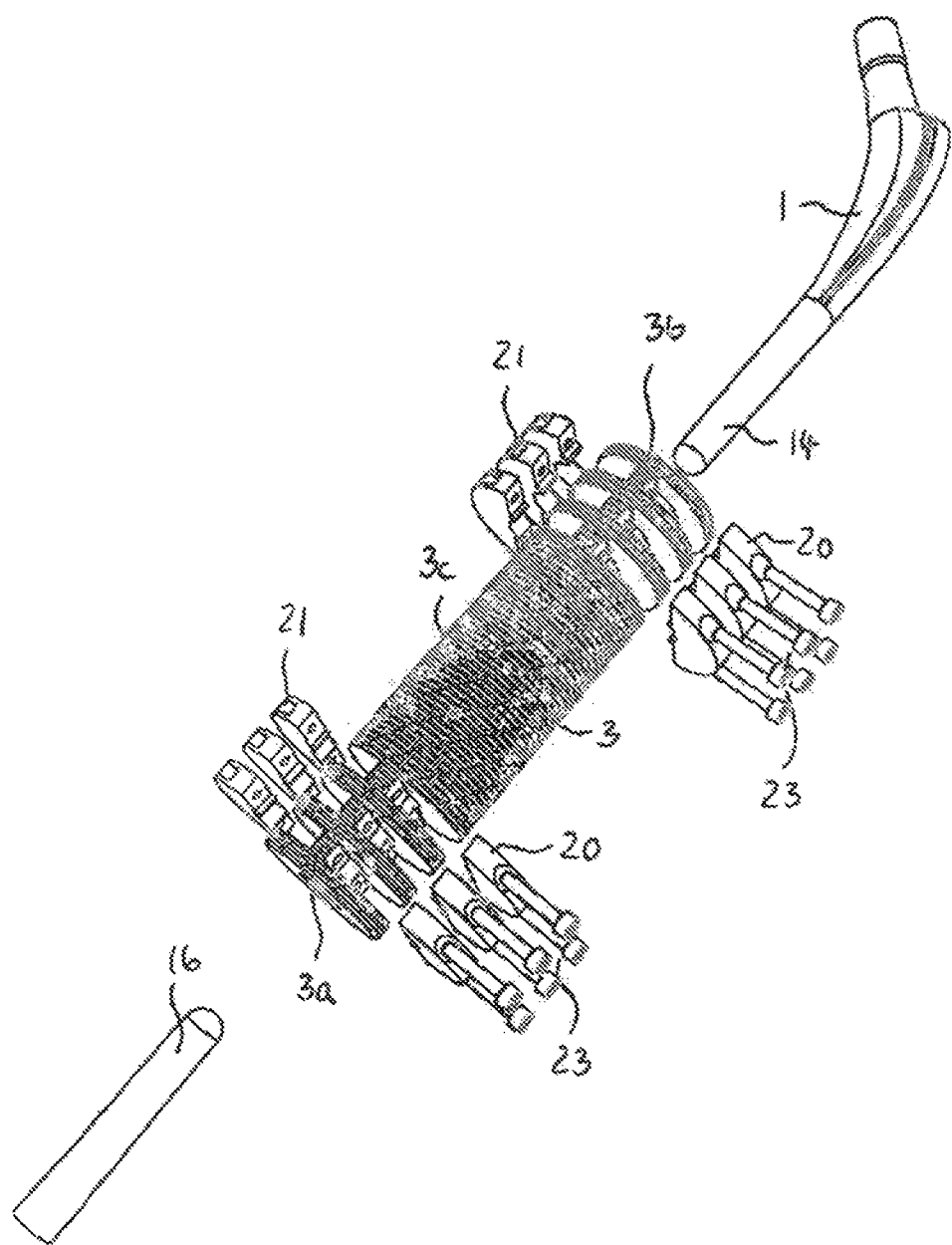
Figure 9:
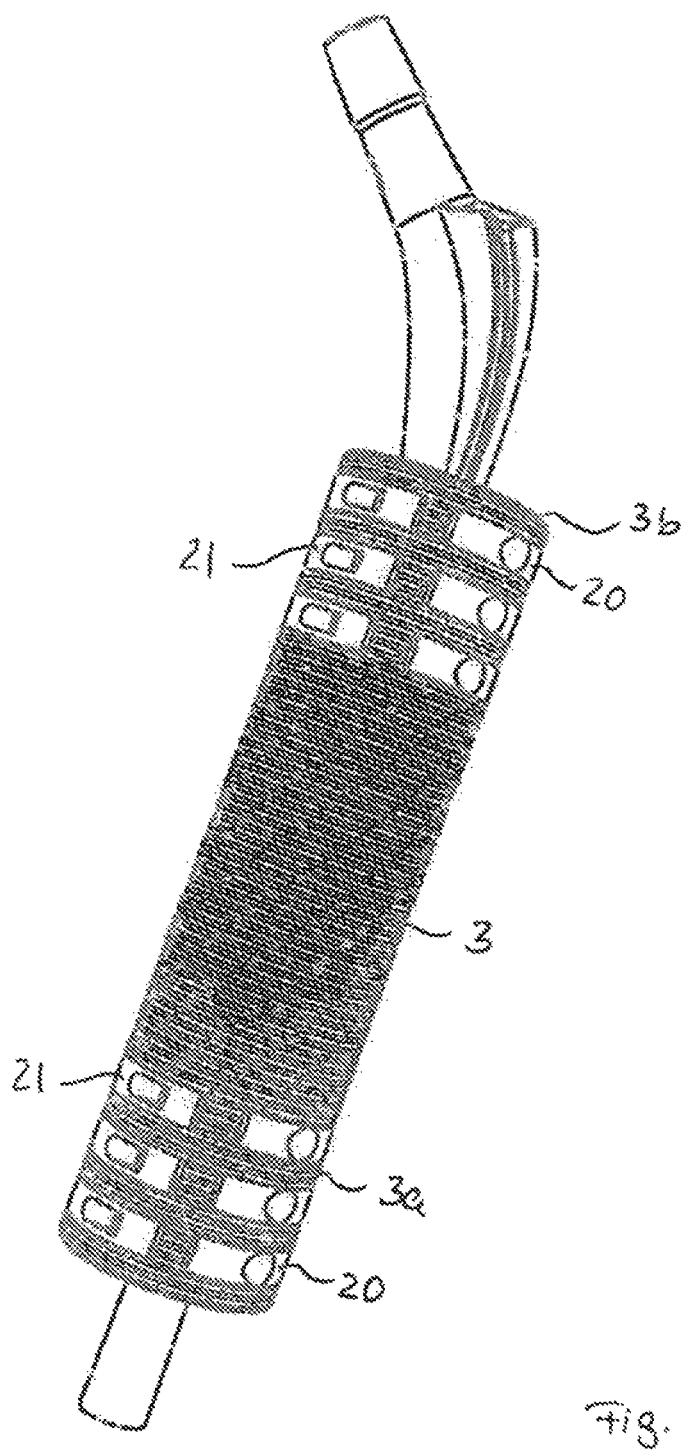
Figure 10:
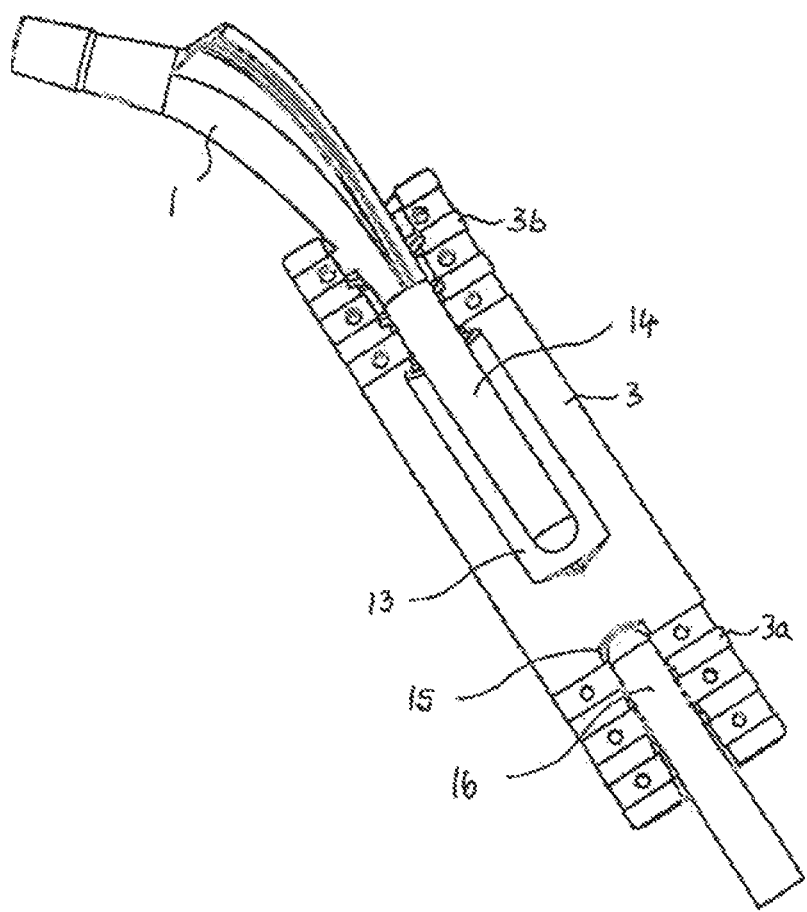
Figure 11:
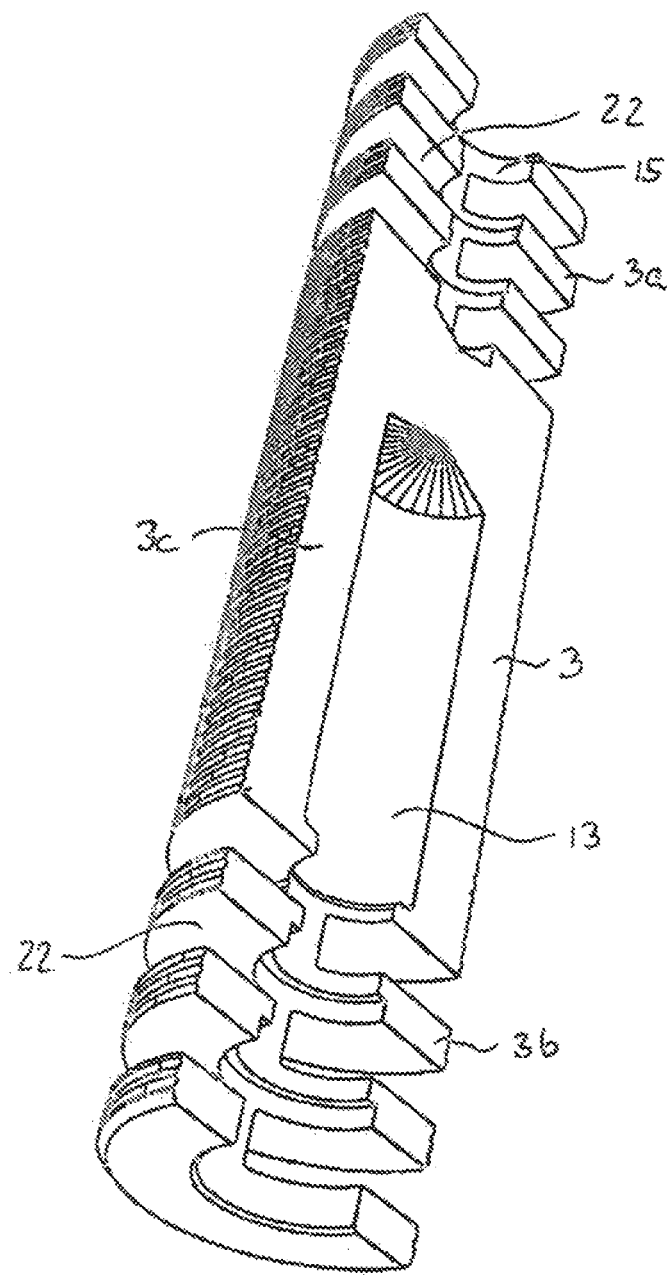
Figure 12:
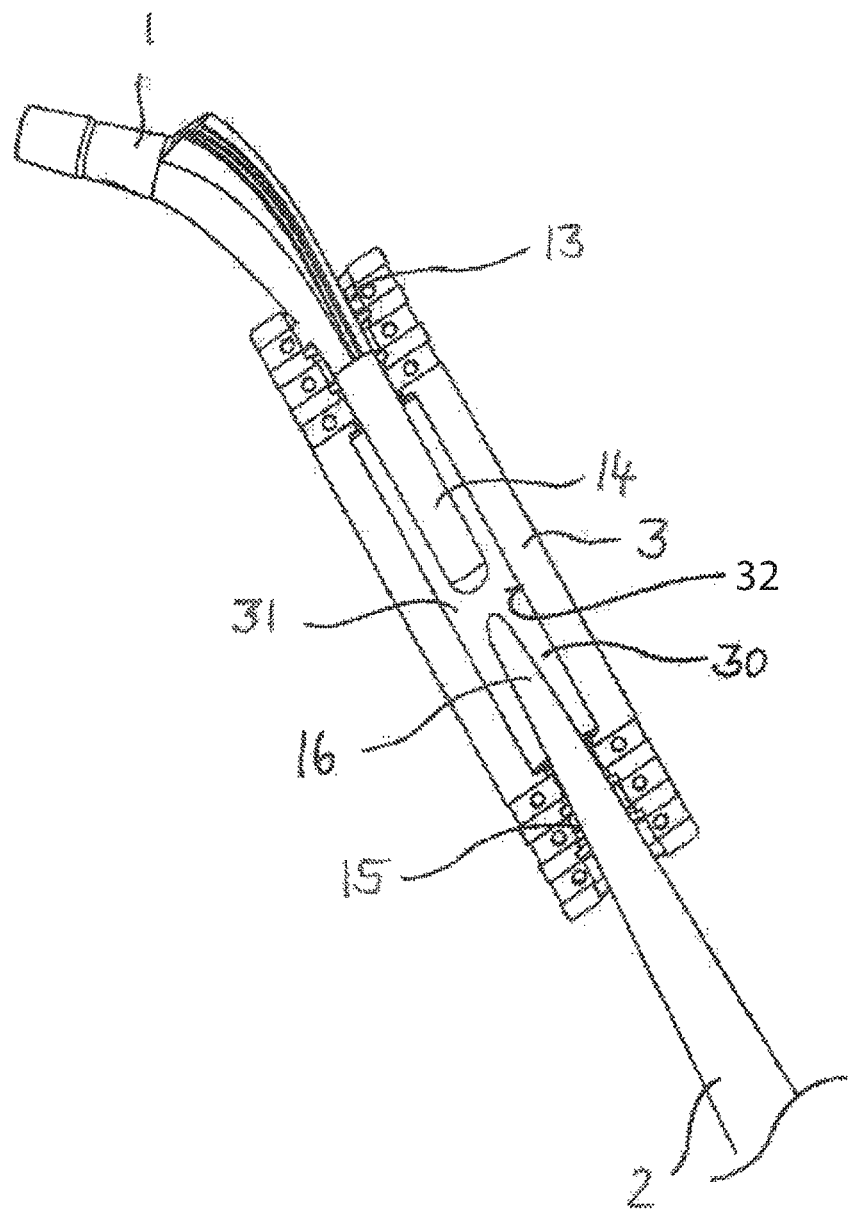

Further illustrative embodiments are explained in more detail below with reference to the figures of a drawing, in which:

FIG. 1 shows a perspective view of an implant arrangement, in particular an endoprosthesis arrangement, with an intermediate body in which end portions of intramedullary implant parts are fixed, FIG. 2 shows a front view of the implant arrangement from FIG. 1, FIG. 3 shows a perspective view of the implant arrangement from FIG. 1 in the unassembled state, FIG. 4 shows a portion of the implant arrangement from FIG. 1 with the intermediate body, FIG. 5 shows a schematic sectional view of the portion from FIG. 4, and FIG. 6 shows a schematic view of a further intermediate body for an implant arrangement, FIG. 7 shows a perspective view of a further implant arrangement with an intermediate body in which end portions of intramedullary implant parts are fixed, FIG. 8 shows a perspective view of the arrangement from FIG. 7, wherein the intramedullary implant parts to be connected are arranged separate from the intermediate body, FIG. 9 shows a view of the further arrangement from FIG. 7, wherein the end portions of the intramedullary implant parts are clamped, FIG. 10 shows a sectional view of the further arrangement from FIG. 7, FIG. 11 shows a perspective sectional view of an intermediate body, and FIG. 12 shows a schematic view of an implant arrangement in which seats for implant parts lie opposite each other and are connected to each other.

Firstly, an implant arrangement designed in the depicted illustrative embodiment as an endoprosthesis arrangement is described below with reference to FIGS. 1 to 6.

FIG. 1 shows a perspective view of an implant arrangement in which a first implant part 1 and a second implant part 2 are rigidly connected to each other at their ends with the aid of an intermediate body 3, wherein the two implants parts 1, 2 in the depicted illustrative embodiment are designed as endoprosthesis parts. The first and second implant parts 1, 2 are provided for an at least partial intramedullary arrangement. Following the implantation, the intermediate body 3 can replace an osseous area in the diaphyseal and/or metaphyseal area of the bone. In the embodiment shown, the first implant part 1 is assigned to a hip-joint prosthesis, whereas the second implant part 2 is a nail implant. This design, however, is shown only by way of example. In principle, any end portions of implant parts can be rigidly connected to each other with the intermediate piece 3, particularly in such a way that the intermediate body 3 of the implant arrangement serves to replace an osseous area in the diaphyseal and/or metaphyseal area of the bone.

FIGS. 2 and 3 show further views of the implant arrangement from FIG. 1. A portion with the intermediate body 3 of the implant arrangement from FIG. 1 is shown from the front in FIG. 4 and in section in FIG. 5.

The intermediate body 3 has a base body 4. In the embodiment shown, the base body 4 has a multi-part design, with a base part 5 and an add-on part 6 which is mounted releasably on the base part 5 with the aid of screws 7. According to FIG. 3, the add-on part 6 in the embodiment shown is designed as a half-shell, which is mounted on an associated portion 8 on the base part 5, the base part 5 likewise being designed as a half-shell, and is secured thereon by means of the screws 7.

The base body 4 has a first base body portion 9 and a second base body portion 10 which, in the example shown, form a respective base body half. While the base body 4 is designed in the first base body portion 9 with a one-part wall 11, the wall 12 in the second base body portion 10 is formed in multiple parts with the aid of the add-on part 6 and of the associated portion 8. The wall 11 in the first base body portion 9 surrounds a first seat 13, which is designed as a receiving pocket. In the assembled state (cf. FIGS. 1 and 2), an end portion 14 of the first implant part 1 engages in the first receiving pocket 13. By comparison, a second seat 15 is formed in the second base body portion 10, in which second seat 15 an associated end portion 16 of the second implant part 2 engages. The second seat 15 is also designed as a receiving pocket. The two seats 13, 15 are separated from each other by a partition wall. 17 (cf. FIG. 5). The first and second seats 13, 15 are surrounded by the respectively associated wall 11, 12, which is part of the base body 4.

The end portion 16 of the second implant part 2 is fixed in the second seat 15 by means of clamping, with the add-on part 6 being screwed onto the associated portion 8 of the base body 4 with the aid of the screws 7. For improved fixing, surface structures 18 that prevent slipping are provided in the second seat 15. In the embodiment shown, the second seat 15 is provided with a cylindrical inner shape.

In contrast to the fixing of the end portion 16 of the second implant part 2 with the aid of the wall portions of the add-on part 6, surrounding the second seat 15, and of the associated portion 8, the end portion 14 of the first implant part 1 is fixed in the first seat 13 with the aid of a clamp device 19 which, according to FIG. 3, is formed with clamp components 20 and mating clamp components 21. After assembly, the clamp components 20 and the mating clamp components 21 are arranged in associated clamp component seats 22 which, in the embodiment shown, are produced correspondingly on the base body 4 in a regular arrangement extending in the axial direction. In the embodiment shown, the clamp components 20 and the mating clamp components 21 are designed as flat components, which are inserted laterally and with a substantial form fit into the associated clamp component seats 22. The clamp components 20 and the mating clamp components 21 are held together with the aid of further screws 23. By means of the further screws 23, the clamp components 20 and the mating clamp components 21 are then also brought jointly toward each other into a respective clamping position, which takes place by means of relative movement with respect to the wall 11 surrounding the first seat 13, such that, finally, the end portion 14 of the first implant part 1 is clamped in the first seat 13.

In the embodiment according to FIG. 3, the clamp components 20 and the mating clamp components 21 have, on the side facing toward the first seat 13, a superficial clamp structure 24 which, as can be seen from FIG. 3, is different at least for the clamp components 20, in such a way that the width or breadth of the superficial clamp structure 24 decreases toward the center of the base body 4. In this way, a conical or tapering matching structure is obtained with the aid of the several mating clamp components 21 in the area of the first seat 13. The clamp components 20 can optionally have a comparable or another superficial clamp structure.

Alternatively, provision can also be made (not shown) that only the clamp components 20 are arranged on the base body 4, whereas the mating clamp components 21 are not provided, in such a way that the wall 11 surrounding the first seat 13 is here complete and closed, with the result that when the end portion 14 is clamped in the first seat 13, it is pressed against the inner wall in the first seat 13 by means of the clamp components 20.

It will be clear from the views in FIGS. 1 to 5 that the screwing direction, and therefore the direction of action, of the screws 7, on the one hand, and of the further screws 23, on the other hand, are transverse to each other.

Whereas in the second base body portion 10, when the add-on part 6 is released, the end portion 16 can be placed from above onto the associated portion 8 in order thereafter to fit the add-on part 6 so as to complete the second seat 15, the end portion 14 of the first implant part 1 is to be pushed or plugged into the first seat 13 via the inlet opening at the end.

Provision can be made (not shown) for clamp components comparable to the clamp component 20 and the mating clamp components 21 to be provided in associated seats also in the area of the second base body portion 10.

FIG. 6 shows a further intermediate body 60 which, comparable to the first base body portion 9 in the embodiment in FIGS. 1 to 5, is provided with clamp component seats 62, but in this case over the entire length of the base body 4. The arrangement of the clamp component seats 62 with associated clamp components 61 extends here over the entire axial length of the intermediate body 60 having seat 63.

A further implant arrangement with an intermediate body is described below with reference to FIGS. 7 to 11. For identical features, the same reference signs are used as in the preceding figures.

In the intermediate body 3 of the implant arrangement in FIGS. 7 to 11, end portions 3$a$, 3$b$ are each formed with clamp component seats 22 into which clamp components 20 and mating clamp components 21 are inserted in order to clamp the end portions 14, 16. In a central area 3$c$, the intermediate body 3 is free of said seats 22.

As will be seen in particular from FIG. 10, the first and second seats 13, 15 are in each case formed as a blind hole. In particular, FIG. 10 also shows that the inserted end portion 14 can optionally extend as far as the center of the implant part 1 or even beyond this, depending on the particular application. In the further implant arrangement, the two seats 13, 15 have a different axial depth.

FIG. 12 shows a schematic view of an implant arrangement, wherein the intermediate piece 3 is depicted in section. The seats 13, 15 are connected to each other, such that a continuous seat 30 is formed. This makes it possible to push both implant parts 1, 2 with a flexible depth of insertion into the continuous seat 30. In a central portion 31, the continuous seat 30 has a constant diameter, in such a way that the end portions 14, 16 in the central portion 31 are free all the way round, i.e. are not in contact with an inner wall 32 in the central area 31.

The features of the invention that are disclosed in the above description, in the claims and in the drawing may be of importance, both individually and also in any desired combination, for the implementation of the invention in its various embodiments.

The invention claimed is:

1. An intermediate body for a bone implant for replacing an osseous area, the intermediate body comprising:

a base body having a seat which extends axially in the base body and is defined by an outer wall surrounding the seat wherein the seat is configured to receive and surround an end portion of an intramedullary implant part, the base body also having at least one clamp component seat extending inwardly from an external surface of the outer wall and including opposed upper and lower walls connected by a portion of the outer wall, and an adjustable clamp arrangement associated with the seat of the base body and including at least one screw element received in the outer wall of the base body and at least one clamp component engageable against the portion of the outer wall, the at least one clamp component receiving the at least one screw element through the at least one clamp component, and configured for movement between a clamped position and a released position relative to the seat of the base body to engage and clamp the end portion of the implant part in the seat of the base body in response to turning of the at least one screw element through the at least one clamp component from outside the base body into at least one bore formed in the portion of the outer wall.

2. The intermediate body of claim 1, wherein the at least one clamp component is connected to at least one mating clamp component by the at least one screw element and configured such that the at least one clamp component and the at least one mating clamp component are brought together by turning the at least one screw element to clamp the end portion of the implant part in the seat.

3. The intermediate body of claim 1, wherein the at least one clamp component is configured for movement relative to the at least one clamp component seat formed in the outer wall of the base body during turning of the at least one screw element.

4. The intermediate body of claim 3, wherein the outer wall of the base body is cylindrical, and the at least one clamp component and the at least one clamp component seat are configured with a semi-cylindrical shape.

5. The intermediate body of claim 1, wherein the at least one clamp component is releasably received in the outer wall of the base body.

6. The intermediate body of claim 1, wherein the at least one clamp component is configured for adjustable movement within the seat of the base body.

7. The intermediate body of claim 1, wherein the adjustable clamp arrangement includes several clamp components attached to several screw elements arranged on the outer wall of and surrounding the seat of the base body, and configured to be moved independently of one another to engage and clamp the end portion of the implant part in the seat of the base body upon turning of the several screw elements.

8. The intermediate body of claim 7, wherein the several clamp components have individual and mutually different clamp component widths which are set in the seat of the base body.

9. The intermediate body of claim 7, wherein the several clamp components form an arrangement of clamp elements extending in an axial direction of the base body.

10. The intermediate body of claim 9, wherein the arrangement of clamp elements is formed along an entire length of the base body.

11. The intermediate body of claim 7, wherein the several clamp components are configured with a superficial clamp structure on a side facing toward the seat of the base body.

12. The intermediate body of claim 7, wherein the several clamp components are connected with several mating clamp components by the several screw elements, and configured such that the several clamp components and several mating clamp components are brought together by turning of the several screw elements to clamp the end portion of the implant part in the seat of the base body.

13. The intermediate body of claim 12, wherein the outer wall of the base body is cylindrical and the several clamp components and the several mating clamp components are configured with a semi-cylindrical shape.

14. The intermediate body of claim 7, wherein the several clamp components have a multi-part configuration.

15. The intermediate body of claim 1, wherein the at least one clamp component is adjustable within the seat of the base body to clamp the end portion of the implant part against the seat of the base body.

16. The intermediate body of claim 1, wherein the at least one clamp component is configured with a clamp surface configured for mating relationship with the end portion of the implant part.

17. The intermediate body of claim 1, wherein an anti-slip surface is formed on an inner face of the outer wall of the base body.

18. The intermediate body of claim 1, wherein the clamp arrangement is formed with tensioning elements configured to provide clamping forces oriented transversely with respect to one another.

19. The intermediate body of claim 1, wherein the at least one screw element is screwed into the outer wall of the base body.

20. An implant arrangement with the intermediate body of claim 1, wherein the end portion of the implant part is inserted into the seat in the base body and fixed therein by the clamp arrangement.

* * * * *